United States Patent
Nekrasov et al.

(10) Patent No.: US 11,364,283 B2
(45) Date of Patent: Jun. 21, 2022

(54) METHOD FOR PRODUCING HYALURONIDASE CONJUGATE WITH POLYETHYLENEPIPERAZINE DERIVATIVES AND THE USE OF THE CONJUGATE PRODUCED

(71) Applicant: OBSHCHESTVO S OGRANICHENNOY OTVETSTVENNOSTYU "NPO PETROVAKS FARM", Pokrov (RU)

(72) Inventors: Arkadii Vasilevich Nekrasov, Moscow (RU); Temuri Musaevich Karaputadze, Moscow (RU); Sergei Alekseevich Medvedev, Moscow (RU); Alexander Vladimirovich Kozukov, Krasnogorsk (RU); Nino Temurievna Karaputadze, Moscow (RU)

(73) Assignee: NPO Petrovax Pharm LLC, Moscow (RU)

( * ) Notice: Subject to any disclaimer, the term of this patent is extended or adjusted under 35 U.S.C. 154(b) by 0 days.

(21) Appl. No.: 15/781,170

(22) PCT Filed: Nov. 9, 2016

(86) PCT No.: PCT/RU2016/000755
§ 371 (c)(1),
(2) Date: Jun. 4, 2018

(87) PCT Pub. No.: WO2017/095264
PCT Pub. Date: Jun. 8, 2017

(65) Prior Publication Data
US 2018/0344815 A1    Dec. 6, 2018

(30) Foreign Application Priority Data

Dec. 4, 2015 (RU) ........................... RU2015152036

(51) Int. Cl.
| | |
|---|---|
| A61K 38/43 | (2006.01) |
| A61K 31/787 | (2006.01) |
| C08F 26/06 | (2006.01) |
| C08F 8/02 | (2006.01) |
| C08F 8/06 | (2006.01) |
| A61K 9/02 | (2006.01) |
| A61K 9/06 | (2006.01) |
| A61K 47/59 | (2017.01) |
| A61P 19/04 | (2006.01) |
| A61P 29/00 | (2006.01) |

(52) U.S. Cl.
CPC ............... *A61K 38/43* (2013.01); *A61K 9/02* (2013.01); *A61K 9/06* (2013.01); *A61K 31/787* (2013.01); *A61K 47/59* (2017.08); *A61P 19/04* (2018.01); *A61P 29/00* (2018.01); *C08F 8/02* (2013.01); *C08F 8/06* (2013.01); *C08F 26/06* (2013.01)

(58) Field of Classification Search
None
See application file for complete search history.

(56) References Cited

U.S. PATENT DOCUMENTS 5,811,100 A    9/1998    Daugalieva

FOREIGN PATENT DOCUMENTS

| RU | 2112542 | 6/1998 |
| RU | 2556378 | 7/2015 |

OTHER PUBLICATIONS

Written Opinion of the International Searching Authority; International Application No. PCT/RU2016/000755, dated Apr. 6, 2017 (6 pgs.).

*Primary Examiner* — Robert J Yamasaki
(74) *Attorney, Agent, or Firm* — Fitch, Even, Tabin & Flannery LLP

(57) ABSTRACT

This disclosure relates to methods for obtaining immobilized enzyme preparations, in particular to a preparation and application of a novel active conjugate of an enzyme with a polymer carrier. Said conjugate possesses the properties of the known Longidaza® drug and inhibits hyperplasia of connective tissue, and presents anti-inflammatory action, and can be used for manufacturing stable, active and safe in use long-acting drugs in the form of a suppository, ointment, injection, cosmetic cream, and for making veterinary drugs. These methods include conjugation of hyaluronidase with a water-soluble copolymer using the carbodiimide or azide conjugation method. The conjugation is carried out with the use of a copolymer N-oxide 1,4-ethylene piperazine, (N carboxymethyl)-1,4-ethylene piperazine or its hydrazide, and 1,4-ethylene piperazine of general formula:

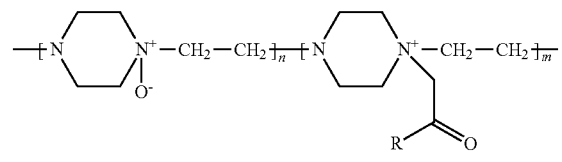

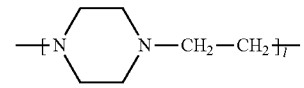

R = OH, NHNH$_2$ where n is from 40% to 90% of the total number of units; m is from 3% to 40% of the total number of units; and n+m+1=100%.

15 Claims, 1 Drawing Sheet

METHOD FOR PRODUCING HYALURONIDASE CONJUGATE WITH POLYETHYLENEPIPERAZINE DERIVATIVES AND THE USE OF THE CONJUGATE PRODUCED

This invention relates to development of technologies for obtaining immobilized enzyme preparations. It can be widely used in various branches of industry, particularly in pharmaceutical industry, for producing stable, active and safe-in-application long-acting medicinal preparations (drugs).

The most effective method of stabilization of compounds of protein or other nature in a physiological solution is a chemical conjugation based on high-molecular carriers [Parveen S, Sahoo S. K., Clin Pharmacokinet. 2006; 45(10), p. 965; Duncan R., PEGylated Protein Drugs: Basic Science and Clinical Applications. Ed.: Birkhauser Basel 2009; Harris J. M, Chess RB. Effect of pegylation on pharmaceuticals. //Nat Rev Drug Discov, 2003, 2(3), p. 214.

Covalent bonding of medicinal proteins with a polymer carrier increases manifold conformational stability of protein molecules and their resistance to the effect of proteases and specific inhibitors, which makes possible the creation of micromolecular bioactive long-acting drugs based on them [Nekrasov A. V., Puchkova N. G., Immunology (Immunologiya), 2006; 27(2), p. 1].

According to present knowledge, there are plenty of polymer carriers used to prepare conjugates with protein and non-protein compounds. The most known are the conjugates based on polyethylene glycol (PEG), used as medicinal preparations [Beilon P. S., Palleroni A. B. /Interferon Conjugates (Conjugaty interferona), Patent RU 2180595. Burg Y, Hilger B., Josel H. P., Patent RU 2232163; Kurochkin S. N., Parkansky A. A., Patent RU 2298560].

There are known water-soluble polymer heterocyclic amines, for example, derivatives of N-oxide poly-1,4-ethylenepiperazine. Polymer amines are unique in their properties and applicability as a polymer carrier for conjugation. A copolymer of N-oxide 1,4-ethylenepiperazineand (N-carboxymethyl)-1,4-ethylene piperazine halogenide (Polyoxidonium®) is non-toxic. It possesses antiradical and detoxification properties, and it is bio-degradable due to the presence of N-oxide groups. This copolymer is allowed for application in medical practice, and it is used as an immune-modulator, adjuvant or polymer carrier [Nekrasov A. V., Puchkova N. G., Ivanova A. S. Derivatives of poly-1,4-ethylene piperazine having immune-modulating, antivirus, antibacterial activities. Patent RU 2073031]. This makes urgent and important the aim of development of easy-to-reach and simple technologies of production of polymer carriers, compliance with all specified requirements, and various conjugation processes on their basis.

Patent RU 2185388 (published on 20 Jul. 2002) describes oxidation of poly-1,4-ethylene piperazine in an aqueous solution containing a solvent and an oxidizer capable of causing a release of oxygen under normal conditions. It is appropriate to use as oxidizers organic and inorganic peroxides and hydroperoxides, salts of oxygenated haloacids, ozone, oxygen, all resulting from water electrolysis. As an acidic solvent, for example, concentrated acetic acid water solution may be used.

It is reasonable to perform oxidation by way of mixing poly-1,4-ethylene piperazine (PEP) with acetic acid (AA) aqueous solution and hydrogen peroxide (HP) in a molecular ratio: PEP:AA:HP=1:0.45:0.7. The oxidation process goes on in a heterogeneous medium until complete dissolution of the polymer is reached. Then, the obtained N-oxide poly-1,4-ethylene piperazine is subjected to alkylation in the presence of an alkylating agent. This process is carried out in aqueous environment. It is recommended to use as an alkylating agent substances that covalently bond with a tertiary nitrogen atom in the polymer chain within a temperature range from 30 to 100° C., for example, haloacids or their ethers of cyclic or acyclic construction.

It is preferable to use bromo-acetic acid ester as the alkylating agent.

The solution of the copolymer of N-oxide poly-1,4-ethylene piperazine and (N-carboxyethyl)-1,4-ethylene piperazine bromide (C-PNO) obtained in the process of alkylation, after it is cleaned, for example, by ultrafiltration, can be used for further synthesis of high-molecular water-soluble biogenic compounds, particularly conjugates or complexes of biologically active substances.

Patent RU 2556378 (published on 10 Jul. 2015) describes the conjugate of a glycoprotein having the activity of erythropoietin and a method of production thereof. Said method includes oxidation of polyethylene piperazine to N-oxide, and alkylation by bromo-acetic acid, resulting in a copolymer of N-oxide poly-1,4-ethylene piperazine and (N-carboxymethyl)-1,4-ethylene piperazine bromide, followed by the cleaning of the obtained copolymer. Copolymer conjugation with erythropoietin is carried out by the carbodiimide or hydrazide method.

The closest to the claimed invention is the invention described in Patent RU 2112542 (published on 10 Jun. 1998). This Patent relates to a drug comprising a conjugate of hyaluronidase enzyme for the treatment of pathological conditions of connective tissues. This Patent describes a method for obtaining a conjugate of hyaluronidase enzyme with a high-molecular carrier—a copolymer of N-oxide poly-1,4-ethylene piperazine and (N-carboxyethyl)-1,4-ethylene piperazine bromide (Polyoxidonium®), mol. wt. 40,000-100,000 D, with an enzyme:carrier ratio of 1:(1-5), corresponding to the general formula:

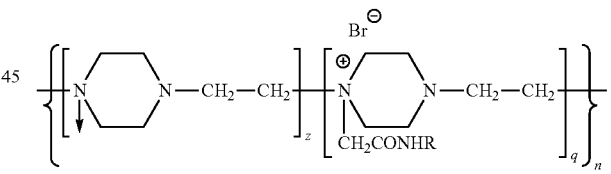

where R is the hyaluronidase enzyme; n=300-700 is the number of elemental units; q=0.2-0.4 is the number of alkylated units; and z=0.4-0.8 is the number of oxygenated units. At the same time, hyaluronidase, segregated from bovine seminal glands, can be used as enzyme in the drug. This method consists of conjugation of hyaluronidase with Polyoxidonium® using either the azide conjugation method or a method of activated succinimide ethers. When using the azide method, the conjugate is obtained in two steps: at the first step, Polyoxidonium® hydrazide is obtained from Polyoxidonium®, and at the second step, the conjugate is obtained by way of a reaction of Polyoxidonium® azide coupling with an enzyme. When using the method of activated succinimide ethers, first, a Polyoxidonium® succinimide ether is obtained, and then it is conjugated with an enzyme. The conjugated drug was named as Longidaza®. The method for obtaining a copolymer of N-oxide poly-1, 4-ethylene piperazine and (N-carboxyethyl)-1,4-ethylene piperazine bromide is not described in the RU 2112542 Patent.

Great demand for preparations having the properties of Longidaza® drug at the pharmaceutical market, economic and environment requirements prompted improvement of the process used for its production with a purpose of ruling out some disadvantages and gaining rise in productivity.

None of the above-mentioned Patents describe the distribution of molecular units in the copolymer structure, or the conjugate obtained on its basis.

The studies revealed that the distribution of molecular units in the copolymer structure exerts an effect upon the properties of the conjugate produced, namely, on the degree of conjugation, outputs of the target product, and stability of the conjugated preparations.

DETAILED DESCRIPTION

Figure 1:
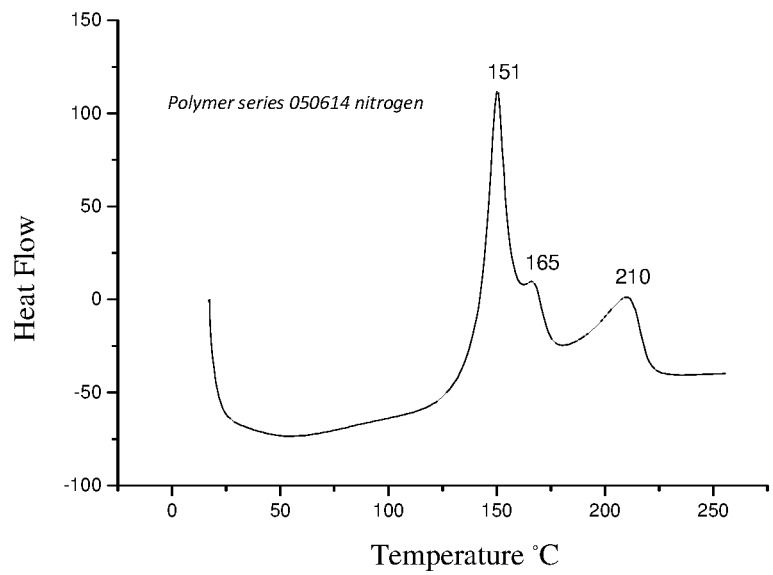
FIG. 1 depicts an exemplary DSC (Differential Scanning Calorimetry) curve for an exemplary polymer (Polymer Series 050614 Nitrogen)

An object of the present invention object is the development of a method for obtaining a conjugate of hyaluronidase enzyme with a polymer carrier comprising the copolymer of N-oxide poly-1,4-ethylene piperazine and (N-carboxymethyl)-1,4-ethylene piperazine bromide having at the same time the properties of inhibition of hyperplasia of connective tissue and anti-inflammatory action, and being fit for the treatment of pathological conditions of connective tissues with improved properties and an increased method of production efficiency.

The assigned task can be solved by a method for obtaining an active conjugate of hyaluronidase enzyme with a copolymer comprising N-oxide 1,4-ethylene piperazine and (N-carboxymethyl)-1,4-ethylene piperazine halogenide using the carbodiimide or azide method of conjugation, followed by cleaning and spray-freeze drying. The conjugation is performed with the use of a water-soluble copolymer, which is a copolymer of N-oxide 1,4-ethylene piperazine, (N-carboxymethyl)-1,4-ethylene piperazine or its hydrazide derivative and 1,4-ethylene piperazine of general formula (I)

presence of urea, alkylation by means of a lower haloalkane acid or its alkyl ether, and hydrazinolysis (in the event that the azide conjugation method is used).

Urea is added at the oxidation step in an amount of 1 to 10 wt. %, preferably 3 to 6%, per total mass of the reaction mixture, water included.

The conjugation is carried out with the use of hyaluronidase taken from bovine seminal glands.

Cleaning is carried out by washing with purified water on a Pellicon® semi-permeable cassette with the lower limit particle cutoff ranging from 1 to 30 kDa.

The copolymer used is a statistical polymer, the units of which in the molecular structure are in a random, disordered state and can be in any order and combination.

The profile of distribution of functional groups influences the polymer carrier reactivity m the conjugation reaction, as well as the stability of the copolymer and the conjugates that are based on this copolymer.

The copolymer derived by using various methods and having the same quantitative characteristics with identical active groups (N-oxide and carboxyl groups) demonstrates absolutely different reactivity in the conjugation reactions. This is due to the fact that carboxyl groups can be difficult to access because of steric reasons and/or may not be activated when N-oxide groups are located adjacently. The usage of a polymer carrier with low-reactive carboxyl groups leads to a significant decrease of conjugation yield and extent, and worsens the molecular weight distribution of the derived conjugates. Up to the present invention, the heterocyclic N-oxide polymer carrier did not have the required number of reactive groups (carboxyl or hydrazide ones), which made it impossible to obtain a reliably high-degree of conjugation by hyaluronidase with an enzyme using the carbodiimide conjugation method or the hydrazide conjugation method. The methods of production described in the present application provide for obtaining hyaluronidase preparations having a degree of conjugation of not less than 90% even on a wholesale scale.

The presence of large segments of a copolymer molecule comprising only N-oxide groups makes a polymer molecule less stable. The stability study demonstrated that conjugates based on such polymer molecules undergo degradation over time. The rate of degradation of a polymer carrier with irregular distribution of N-oxide groups is not constant, and the degradation occurs rather quickly during the first months of storage. On the contrary, a polymer carrier having a uniform distribution of N-oxide groups is much more stable, and its degradation rate is slower and constant. The stability

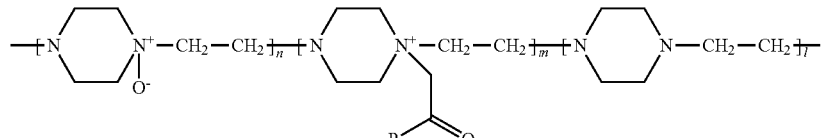

R = OH, NHNH$_2$ where:
n is from 40% to 90% of total number of units;
m is from 3% to 40% of total number of units; and
n+m+1=1000%,
which is obtained from poly-1,4-ethylene piperazine via oxidation by means of an oxidizing agent that is able to cause a release of oxygen under normal conditions in the of the conjugate and the uniformity of the N-oxide groups distribution in the polymer carrier also depends on the conditions of the method of production of the copolymer for conjugation (see Table 1 and Table 2).

The invention described herein relates to the method for production of hyaluronidase conjugates and provides for production of a polymer carrier having not only preset quantitative data (quantity of various units in a polymer), but the required distribution of units, which qualitatively changes the properties of both the polymer carrier and the conjugate with an enzyme that it based on it.

The invention described herein makes it possible to produce a safe, high-efficiency and stable medicinal preparation (drug) possessing the properties of simultaneously inhibiting connective tissue hyperplasia and having anti-inflammatory action, and representing a conjugate of hyaluronidase (a therapeutic enzyme taken from bovine seminal glands) and water-soluble copolymer of general formula (I).

In the event that the azide method of conjugation is used, alkylation is carried out with the use of alkyl ether of haloalkane acid, and the alkylation step and the hydrazinolysis are combined. The conjugation with hyaluronidase is performed by the azide method at temperatures ranging from 0 to 25° C.

Cleaning is a three-fold stepwise washing with purified water on a Pellicon® semi-permeable cassette (with a lower limit particle cutoff ranging from 1 to 30 kDa) upon finishing the oxidation, the alkylation and hydrazinolysis, and the conjugation steps.

The conjugation is carried out with the use of a water-soluble copolymer of general formula (I) comprising in its chain from 3 to 20% hydrazide groups.

In the case of the carbodiimide method of conjugation, poly-1,4-ethylene piperazine is first alkylated and then subjected to oxidation in an aqueous environment. In this process, the alkylation is performed by using a haloalkane acid.

When the carbodiimide conjugation method is used, the cleaning is done in a stepwise manner by washing with purified water on Pellicon® semi-permeable cassettes (with a lower limit particle cutoff ranging from 1 to 30 kDa) upon finishing the steps of obtaining the copolymer and the conjugation.

The conjugation is carried out using a water-soluble copolymer of N-oxide poly-1,4-ethylene piperazine of the general formula (I) comprising in its chain up to 25% carboxyl groups, and using any of the water-soluble carbodiimides in an amount from 3 to 50% from the copolymer involved in the reaction.

An object of the invention is also an active ingredient of the conjugate, possessing the properties of inhibiting hyperplasia of connective tissue as well as anti-inflammatory action, which is produced by any of the described methods for preparation of a medicinal agent in a finished dosage form selected from a suppository, ointment, injection, or cosmetic cream, as well as drugs for veterinary.

Provided below is the detailed description of the claimed method using the azide and carbodiimide methods of conjugation in the production of Longidaza® having particular properties described in detail in 10 Examples below and presented in Table 1.

The conditions of the described technology of production of the polymer carrier and the hyaluronidase conjugates, as it was found, result in a desired distribution of functional units in the copolymer structure, wherein the polymer carrier and the conjugates based thereon become stable in the process of long-term storage. Said result is achieved by performing the reaction of polyethylene piperazine oxidation under dissociating conditions by way of adding urea. With that, non-covalent intermolecular bonds of polyethylene piperazine get destroyed, and the reactions involve separate polymer molecules, rather than molecules in the composition of a micelle, resulting in the desired uniform distribution of functional groups along the polymer chain, increased enzyme activity (by 30 to 65%, see Table 1), the conjugation degree and target product yield (by 15 to 20%, see Table 1), and stability of hyaluronidase conjugate. The enzyme activity of Longidaza® preparations kept in storage at a temperature of 2 to 8° C. within 1 year dropped by 4-6% for the specimens obtained with the use of urea, and by 24-27% without use of urea (Table 1, Example 4 and Example 9).

The conjugate is produced by the following two methods:
the method for hyaluronidase conjugate production using the azide method of conjugation; and
the method for hyaluronidase conjugate production using the carbodiimide method of conjugation.

Poly-1,4-ethylene p1perazm (PEP) with molecular weight from 20 to 60 kDa is used as a feedstock for all methods of production.

PEP results in from cationic polymerization, which is an efficient method of synthesis of monodisperse high-molecular compounds having a preset molecular weight and structure.

1. Method for production of the conjugate using the azide method of conjugation.

This production method consists of the basic steps of the process, namely, oxidation in the presence of urea, alkylation, hydrazinolysis, and conjugation using the azide method.

Oxidation of poly-1,4-ethylene piperazine is carried out in an acidic medium by adding hydrogen peroxide in the presence of urea at a temperature of 45 to 55° C. for 12 to 24 hours in a water-jacketed reaction vessel. Then, the reaction mixture is diluted, filtered in a cartridge filter provided with a filtering element having a pore size of 0.45 nm, and sent to a diafiltration in an ultrafiltration unit with Pellicon® semi-permeable cassettes having a lower limit particle cutoff of 5 kDa, and is then filtered in a cartridge filter provided with a filtering element having a pore size of 0.22 nM.

Thereafter, the resultant product is dried, and tested for compliance with the regulatory document requirements and turn in for storage.

At the second step, N-oxide poly-1,4-ethylene piperazine undergoes alkylation by adding an ether of haloalkane acid in a water-organic solution (a mixture of water and N-methyl formamide) with agitation at a temperature of 35 to 50° C. for 4 to 6 hours, and then, the hydrazinolysis of the achieved alkyl derivative of polyethylene piperazine is by adding hydrazine hydrate at temperatures of 2 to 8° C. The reaction mixture is filtered in a cartridge filter provided with a filtering element having a pore size of 0.45 nm, then the reaction mixture undergoes cleaning in an ultrafiltration unit with Pellicon® semi-permeable cassettes having a lower limit particle cutoff of 10 kDa (percentage of hydrazine hydrate not exceeding 0.001%), after which the reaction mixture is subjected to sterilizing filtration in a cartridge filter and reconstituted in glass vials. Finally, the reaction mixture is tested for compliance with the requirements of the regulatory document and turned in for storage.

At the last (third) step of the process of conjugation of hyaluronidase with a hydrazide compound of carboxymethyl-containing N-oxide polyethylene piperazine comprising in its chain more than 3% of hydrazide groups is performed using the azide method by treatment with sodium nitrite at pH=0-1 and subsequent conjugation of the azide derivative with hyaluronidase for 18 to 22 hours at room temperature. The hyaluronidase conjugate is then filtered, cleaned by washing in an ultrafiltration unit (Pellicon® semi-permeable cassettes with a lower limit particle cutoff of 5 kDa), filter-sterilized, and spray-freeze dried (lyophilized). Test results are shown in Table 1 (Examples 1-3).

The above-described production method, which includes the steps of alkylation, oxidation (but without urea addition), hydrazinolysis, conjugation by the azide conjugation method and cleaning, is used to obtain a Longidaza® specimen. The results of the testing of this specimen are presented in Table 1 (Example 4). The comparative studies demonstrate that addition of urea increases the enzyme activity, the degree of conjugation, the yield of target product, and the conjugate stability (Table 1).

The derived freeze-dried (lyophilized) product is reconstituted in glass vials and turned in for storage in the form of an active conjugate ingredient having the activity similar to that of Longidaza®.

Further, the obtained active pharmaceutical ingredient is used for production of a liquid or freeze-dried injectable drug dosage form. In this regard, the solution is diluted to ensure that in 1 ml of solution, the enzyme activity is 3,000 IU (therapeutic dose), and it is tested in all parameters for compliance with the regulatory requirements for the finished-drug-dosage form. After that, the solution can be freeze-dried (lyophilized medicinal preparation) or, without drying, the liquid medicinal preparation may get packaged, labeled and tested in all parameters for compliance with the regulatory requirements for the finished-dosage form.

The carbodiimide method, described in the present invention, makes possible the performance of a process without use of organic solvents or harmful reagents, and results in the end product, i.e., the hyaluronidase conjugate with derivatives of polyethylene piperazine, having an improved quality and a higher stability.

2. Method of Longidaza® Production with the Use of Carbodiimide Method of Conjugation.

The sequential production process comprises several steps, namely, alkylation, oxidation in the presence of urea, and conjugation using the carbodiimide method.

A poly-1,4-ethylene piperazine with preset properties (see above) is alkylated by bromo-acetic acid in an aqueous environment at a temperature of 40 to 95° C. and a weight ratio (85:15)-(70:30), respectively. The reaction mixture is mixed at a temperature of 50 to 70° C. for 3 hours, then urea, acetic acid and nitrogen peroxide are added to the reaction mixture, and thereafter the reaction mixture is continuously stirred for 18 to 22 hours. Then, the oxidation process completeness is checked with the aid of the ammonia test (similar to Example 1).

The reaction mixture is then filtered in a cartridge filter provided with a filtering element having a pore size of 0.45 nm. The polymer is cleaned by washing in an ultrafiltration unit with Pellicon® semi-permeable cassettes having a lower limit particle cutoff of 5 kDa to a nitrogen peroxide content of not more than 0.001% (the nitrogen peroxide content test). The solution is then concentrated to 10-15%, the content of carboxyl groups in the polymer being less than 6%. A calculated amount of hyaluronidase is introduced into the reaction medium, while stirring, to bring up the pH to a value of 4.8.

While stirring, a water-soluble carbodiimide is added to ensure that its content is 25 to 50% of the added hyaluronidase (expressed as protein). The reaction mixture is kept at a temperature of 0 to 25° C. for 1 to 1.5 hours, and then the degree of conjugation is checked (which shall be not less than 95%). In case of a positive result, the reaction mixture is washed with purified water, alkalified to pH=6.8 to 7.0 and filtered in a disc filter equipped with an AP-15 deep-bed filter. After prefiltration, the reaction mixture cleaning is continuing by washing with purified water on a Pellicon® semi-permeable cassette to ensure that the total amount of water would be at least 200 liters per 1 kg of dry matter. Then, the solution ingredient having the Longidaza® activity is concentrated, sterile filtered in a cartridge filter fitted with a filtering membrane with a pore size of 0.22 nm and reconstituted in glass vials in the form of a liquid ingredient. The resultant sterile concentrate can also be freeze-dried to obtain an ingredient having an activity similar to that of the Longidaza® preparation in a dry state. Thereafter, the resultant concentrate is checked for compliance with applicable regulatory requirements and turned in for storage as an end product. The ingredient test results are provided in Table 1 (Examples 6 to 8).

The above-described production method, which includes the steps of alkylation, oxidation, but without urea addition, conjugation by the carbodiimide method and cleaning procedure, was used to obtain the Longidaza® specimen, the test results of which are presented in Table 1 (Example 9). In the same way as for the case of the Longidaza® production with the use of the azide method of conjugation, urea addition increases the enzyme activity, conjugation degree and target product yield, as well as the stability of the conjugate (Table 1, Table 2).

A sterile solution of the hyaluronidase conjugate can be used for an intended administration purpose. The resultant active pharmaceutical ingredient can be used for the preparation of liquid or freeze-dried injectable dosage forms. With this in view, this solution is diluted to ensure that, in 1 ml of solution, the enzyme activity is 3,000 IU (therapeutic dose) and reconstituted in glass vials and freeze-dried (lyophilized medicinal preparation) or, without drying, the liquid medicinal preparation is packaged, labeled and tested in all parameters for compliance with the applicable regulatory requirements for the finished-dosage form.

In the process of obtaining the hyaluronidase conjugate with polyethylene piperazine derivatives, the ultrafiltration cleaning on Pellicon® semi-permeable cassettes with a particle cutoff of 1 to 30 kDa is used to remove process impurities. Washing is done on completion of the alkylation and oxidation steps, and at the end of the production process. The above-described carbodiimide method of conjugation can be carried out exclusively in an aqueous environment.

Thus, the essence of the above-described method results in a new approach in the technology of production of immobilized compounds on a polymer carrier of a new class in the form of water-soluble PEP derivatives as per the azide and carbodiimide conjugation methods. The copolymer is obtained by chemical modification of PEP in the presence of urea, which in the process of conjugation significantly boosts the hyaluronidase activity, degree of conjugation, and yield of a preparation having the activity and storage stability identical to Longidaza®. An analysis of the results of production of the hyaluronidase conjugate using derivatives of polyethylene piperazine presented in Table 1 (Examples 1 thru 10) indicates a high yield of the target product. Also, the process with the use of the carbodiimide method provides for a higher degree of conjugation and end product activity, and the process can be carried out exclusively in aqueous environment.

The inventive step of the developed methods of production of the hyaluronidase conjugate with derivatives of polyethylene piperazine may be verified by an absence in this business segment profile of continuous processes, and by the fact that production of N-oxide polyethylene piperazine in the methods described herein is carried out with the use of urea. In an industrial setting, the carbodiimide method is more preferable than the azide method. The employment of the methods described herein in production of long-acting forms of compounds of various applications improves the production of a new preparation having an activity higher than the activity of the Longidaza® preparation.

A study of the decomposition of copolymers of N-oxide 1,4-ethylene piperazine, (N-carboxymethyl)-1,4-ethylene piperazine and 1,4-ethylene piperazine has shown that, at a temperature not above 70° C. in an aqueous environment with a pH not exceeding 9, the decomposition occurs exclusively over the N-oxide units. The thermal decomposition of the N-oxides proceeds by way of Meisenheimer rearrangement.

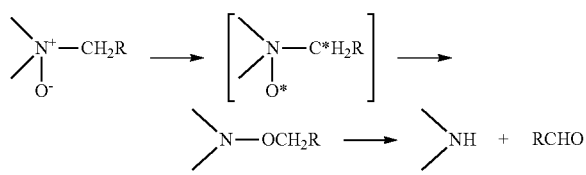

A copolymer having a uniform distribution of various units should not have large portions consisting of units of only one type. Thus, having an N-oxide unit content of 50% or more and their uniform distribution along the polymer chain, the copolymer should not have large portions composed of only unsubstituted units of 1,4-ethylene piperazine (units 1). In light of this, there has been developed a method of qualitative and quantitative evaluation of the uniformity of distribution of the units comprising N-oxide groups along the copolymer chain. The method comprises a copolymer controlled decomposition with subsequent physical-chemical analysis of the resultant fragments. It was found that with the use of urea in the process of oxidation, the decomposition products do not contain the low-molecular polymer comprising units of the following type:

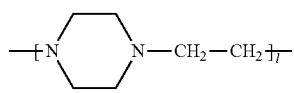

where l=3 and above.

The presence of the above-reproduced substance in the copolymer decomposition products is indicative of significant non-uniformity of the distribution of the N-oxide units in the starting copolymer.

When analyzing a copolymer of series 111114 using the decomposition method, the following substance was extracted:

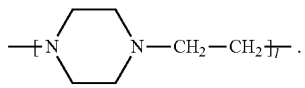

where l = from 4 to 6

Upon completion of a quantitative and qualitative analysis of the composition of this substance, one can evaluate the qualitative and quantitative profile of the distribution of the N-oxide groups in the studied copolymer. However, the developed measuring procedure is time consuming (the monitored decomposition of the N-oxide groups of the copolymer takes 5 weeks) and a large amount of the substance needs to be analyzed. With this in view, a qualitative method for rapid assessment of the uniformity of distribution of the units was designed.

The analysis of various specimen of copolymers using the DSC (Differential Scanning Calorimetry) method demonstrated that polymers of this type vigorously degrade at a temperature of about 160° C. while releasing heat. At the same time, different forms of the exotherm peak of decomposition were observed in specimen produced with and without added urea. Thus, two specimen of a polymer carrier were observed having similar quantitative parameters, namely, molecular weight, molecular-weight distribution, number of carboxyl and N-oxide groups produced with the addition and without the addition of urea at the oxidation step. In this case, the conjugates, obtained on one polymer carrier, were stable, and those obtained on another carrier were not stable.

Figure 2:
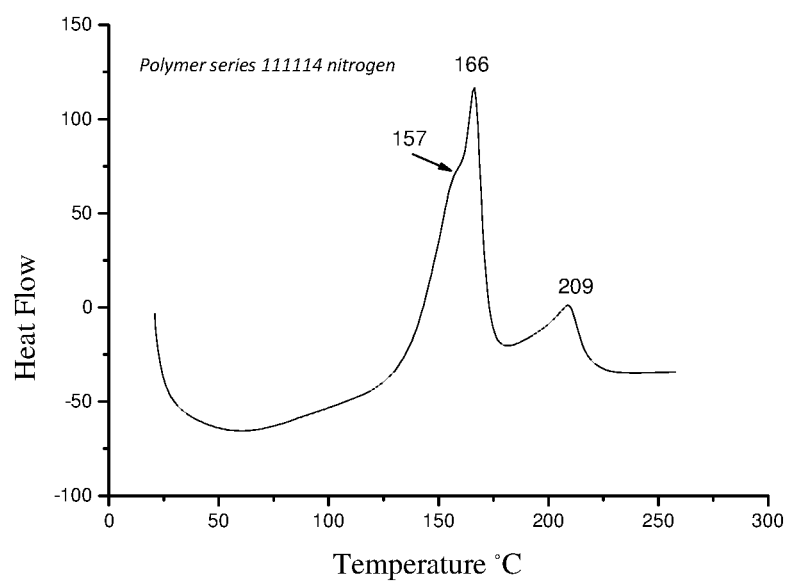
FIG. 2 depicts an exemplary DSC (Differential Scanning Calorimetry) curve for another exemplary polymer (Polymer Series 111114 Nitrogen).

The DSC curves for polymers are shown in FIGS. 1 and 2.

The DSC curves (FIGS. 1 and 2) demonstrate significant differences in the ratio of peak intensities within a temperature range of 150 to 170° C. The obtained results indicate a relation between the polymer structure (units distribution profile) and its thermal stability. The received results were verified by analysis of other carriers, and they demonstrate a possibility of distinguishing the specimen of polymer carriers with different stability due to the functional groups arrangement in the molecule of a polymer carrier.

Provided below are the particular parameters accumulated in Table 1 and presented in Examples 1-3 and 6-8. Table 1 also presents the results of a commercial scale series (Example 5 and Example 10). Examples 4 and 9 contain data verifying the advantages of the method of production in the presence of urea.

EXAMPLE 1

The method of production of a hyaluronidase conjugate with derivatives of polyethylene piperazine using the azide method of conjugation. Initially, 200 grams of shavings of poly-1,4-ethylene piperazine (PEP) with a molecular weight of 50 kD, which were pre-chopped and cleaned by a method of quadruple washing with purified water, are oxidized in a mixture of 50 ml of acetic acid, 140 ml of 30-% solution of hydrogen peroxide in water, and 50 grams of urea. Water is added in such a way that the PEP content is 15 wt. %, i.e., and the volume of the reaction medium is 1.5 liters. The reaction mixture is heated up to 50° C. and continuously stirred for 24 hours. The oxidation completeness is checked with the aid of ammonia testing. This testing is performed as follows: 10 ml of 25% solution of ammonia are added to 1 ml of the reaction mixture. The absence of turbidity in solution, after not stirring the solution for 20 minutes, is considered as a positive result. In case of a positive result, the reaction mixture is diluted, filtered in a cartridge filter fit with a filtering element with a pore size of 0.45 nm, cleaned and concentrated in an ultrafiltration unit with Pellicon® ultrafiltration cassettes having a lower limit of particle cutoff of 5 kDa, and filtered in a cartridge filter equipped with a filtering element with a pore size of 0.22 nm. Thereafter, the filtered reaction mixture is freeze-dried, resulting in 204 grams of N-oxide poly-1,4-ethylene piperazine in the form of a lyophilizate, which is checked for compliance with the applicable regulatory requirements and turned in for storage.

The resultant N-oxide poly-1,4-ethylene piperazine lyophilizate is dissolved in 1,500 ml of distilled water, and 6,000 ml of N-methyl formamide is added. 275 ml of bromoalkene ether is added to the resulting solution while continuously stirring at temperatures of 35-50° C. for 4 to 6 hours. Then, the reaction mixture is cooled down to 2-8° C. and, while continuously stirring, 250 ml of hydrazine hydrate is added to the reaction mixture. The reaction mixture is diluted 10 times with purified water, filtered in a cartridge filter fit with a filtering element with a pore size of 0.45 nm, and cleaned by washing on Pellicon® semi-permeable cassettes having a lower limit of particle cutoff of 10 kDa until only trace amounts (not more than 0.001%) of hydrazine hydrate remain in the reaction mixture. Further, the reaction mixture is concentrated to 10-12% (as per target substance), sterile filtered, and reconstituted in glass vials. Thus obtained is a solution of 2,200 ml of hydrazide derivative of N-oxide poly-1,4-ethylene piperazine, which is analyzed for compliance with the applicable regulatory requirements and turned in for storage.

The solution obtained during the previous step is cooled down to 2 to 6° C. and, while the solution is being stirred and cooled, hydrochloric acid is added to bring the pH to 0-1. Then, with stirring and cooling continued, 360 grams of sodium nitrite is added in batches and the reaction mixture is allowed to stand for 1.5 hours. After that, the reaction mixture is rendered alkaline by adding moist-free ash to bring the pH to 6.8-7 and, at a temperature not exceeding 10° C., while stirring, a 10% solution, which contains 65 grams of hyaluronidase (70% of protein), is added. The reaction mixture is stirred for 1.5 hours, after which a sample is taken to check the conjugation degree. In case the conjugation degree check indicates a positive result (i.e., not less than 70% conjugation), the reaction mixture is filtered in a disc filter fitted with a deep AP-15 type filer, and washed in 50 liters of purified water in an ultrafiltration unit with Pellicon® semi-permeable cassettes having a lower limit particle cutoff of 5 kDa. The solution is concentrated, sterile filtered and filled in sterile glass vials (liquid substance). The sterile solution is also freeze-dried and packed in sterile glass vials (lyophilized substance). Thus obtained are 231 grams of the lyophilized substance, with a 86% yield. The results of testing the obtained conjugate substance are presented in Table 1 (Example 1). The resultant substance is used for preparation of a finished medicinal product with a type of activity that is identical to that of the known "Longidaza®" preparation, administered in the form of a vaginal and rectal suppository of 3,000 IU.

EXAMPLE 2

The procedure is similar to that of Example 1, with the difference being that 200 g of purified PEP shavings with a molecular weight of 40 kDa are used, and that 60 grams of urea are used at the oxidation step. The procedure results in 227 grams of a lyophilized substance (84% yield) having a type of activity that is identical to the activity of the known Longidaza® preparation. The analysis results are presented in Table 1, Example 2. The resultant lyophilized substance is used for preparation of creams and ointments for external use, 1000 IU.

EXAMPLE 3

The procedure is similar to that of Example 1, with the difference being that 200 g of purified PEP shavings with a molecular weight of 55 kDa are used, and that 80 grams of urea are used at the oxidation step. The procedure results in 235 grams of a lyophilized substance (87% yield) with a type of activity that is identical to the activity of the known Longidaza® preparation. The analysis results are presented in Table 1, Example 3. This lyophilized substance is used for preparation of an injectable dosage form.

EXAMPLE 4

The procedure is similar to that of Example 1, with the difference being that urea is not added at the oxidation step. The resultant lyophilized substance amounting to 215 grams (74% yield) has an activity of a type that is identical to that of the known drug Longidaza®. The results of Longidaza® testing are given in Table 1, Example 4. The lyophilized substance is used for preparation of an injectable dosage form.

EXAMPLE 5

The procedure is similar to that of Example 1, with the difference being that 4,000 g of chopped and purified PEP with a molecular weight of 45 kDa are used, and that 2,000 grams of urea are used at the oxidation step. This procedure results in 4,700 grams of a lyophilized substance (87% yield) having a type of activity that is identical to the activity of the known Longidaza® preparation. The test results are presented in Table 1 (Example 5). Batching up required amounts of the produced lyophilized substance in suppository, ointment or cream bases, results in suppositories, creams, and ointments, respectively, comprising the active ingredient. The lyophilized substance is also used for preparation of injectable dosage form.

EXAMPLE 6

The method uses the carbodiimide method of conjugation. Poly-1,4-ethylene piperazine (PEP) in an amount of 200 g with a molecular mass of 30 kDa is added to 1.2 liters of boiling-water solution comprising 58 grams of bromo-acetic acid, and is heated at a temperature of 70° C. for 3 hours, while being continuously stirred. Then, 40 ml of acetic acid, 140 ml of 30% water solution of nitrogen peroxide, and 50 grams of urea are added to the reaction mixture and all are stirred at a temperature of 38-42° C. for 18 to 20 hours. Further, the oxidation state completeness is checked with the aid of the ammonia test (this test is described above). In the case of a positive result during the ammonia test, the reaction mixture is diluted to a concentration of 1 to 2%, and filtered in a cartridge filter that is fitted with a filtering element having a pore size of 0.45 nm, followed by cleaning by washing with purified water on a Pellicon® semi-permeable cassette having a lower limit particle cutoff of 5 kDa.

During washing, the solution is rendered alkaline to a value of pH=11.0-11.5 with the purpose of a complete cleaning to remove traces of low molecular weight organic acids. The cleaning of the solution is continued until the hydrogen peroxide content becomes not more than 0.001% (checked by the hydrogen peroxide test), and the solution is concentrated to 10% of the target substance. The resultant solution is acidified by hydrochloric acid to a pH=4.8-4.9, after which 50 grams of hyaluronidase are added. If necessary, the pH value is again adjusted so that the pH value is 4.8 to 4.9. Then, a solution comprising 2.1 grams of N-(3-dimethylaminopropyl)-N'-ethyl carbodiimide hydrochloride in 210 ml of water is added to the reaction mixture followed by stirring for 1.5 to 2 hours. The conjugation reaction is carried out at a temperature of 2 to 25° C.

After adding the last portion of a condensing agent solution, the reaction mixture is allowed to stand while being stirred for 30 minutes at a preset temperature, and a sample is taken to determine the conjugation degree. In the case of a positive result indicating that the conjugation degree is at least 90%, the reaction mixture is allowed to stand for 18 to 20 hours, and is rendered alkaline by means of a moist-free ash to a value of pH=6.8 to 7.0, after which it is washed and filtered using a disc filter with a filtering material in the form of a deep AP-15 type filter. Then, the reaction mixture is cleaned by purified water in an ultrafiltration unit on a Pellicon® semi permeable cassette with a lower limit particle cutoff equal to 5 kDa. The cleaned solution is concentrated to a content of 8-10%, and sterile filtered in a cartridge filter fitted with a filtering element having a pore size of 0.22 nm. The resultant solution of hyaluronidase conjugate with derivatives of polyethylene piperazine can be diluted to a concentration containing 3,000 IU of enzyme activity in 1 ml of solution, finally obtaining an injectable dosage (liquid) form or freeze-dried (lyophilized) form. In the case of freeze-drying, the method results in 261 grams of a lyophilized substance (97% yield) having a type of activity that is identical to the activity of the known Longidaza® preparation. The test results are presented in Table 1, Example 6.

Batching up the required amount of the produced lyophilized substance in a suppository base results in suppositories.

EXAMPLE 7

The procedure is similar to that of Example 6, with the difference being that 200 g of purified PEP shavings with a molecular weight of 38 kDa are used, and that 60 grams of urea are used at the oxidation step. This procedure results in 265 grams of a lyophilized ingredient (98% yield) having a type of activity that is identical to the activity of the known Longidaza® preparation.

Test results are presented in Table 1, Example 7.

This ingredient is used for the preparation of an ointment.

EXAMPLE 8

The procedure is similar to that of Example 6, with the difference being that 200 g of purified PEP shavings with a molecular weight of 26 kDa are used, and that 70 grams of urea are used at the oxidation step. This procedure results in 264 grams of a lyophilized substance (98% yield) with a type of activity that is identical to the activity of the known Longidaza® preparation.

Test results are presented in Table 1, Example 8.

This lyophilized substance is used for preparation of an injectable dosage form.

EXAMPLE 9

The procedure is similar to that of Example 6, with the difference being that 200 g of purified PEP shavings with a molecular weight of 26 kDa are used, and that at the oxidation step no urea is added. This procedure results in 217 grams of a lyophilized substance (82% yield) with a type of activity that is identical to that of the known Longidaza® preparation.

The test results are presented in Table 1, Example 9.

The lyophilized substance is used for the preparation of an injectable dosage form comprising Longidaza®.

EXAMPLE 10

The procedure is similar to that of Example 6, with the difference being 4,000 g of purified PEP shavings with a molecular weight of 36 kDa are used, and that at the oxidation step 1,500 grams of urea is added. The procedure results in 5,130 grams of a lyophilized substance (95% yield) with a type of activity that is identical to that of the known Longidaza® preparation. The test results are presented in Table 1 (Example 10). Batching up the required amount of produced ingredient in suppository, ointment, and cream bases results in suppositories, creams, and ointments, respectively, comprising the active ingredient. The lyophilized substance is also used for preparation of injectable dosage form.

The claimed continuous carbodiimide method makes it possible to exclude from the process organic solvents, to simplify the process, upgrade the quality and increase the target product yield, to achieve a high degree of conjugation, and increase the stability of Longidaza® (in freeze-dried and liquid form) under its exposure to various environmental effects during processing and storage. The described methods provide for improvement of processes of production of long-acting conjugates based on the new class carriers of compounds in the form of water-soluble derivatives of heterocyclic aliphatic aminopolymer N-oxides, comprising in their chain azide or carboxyl groups, and non-stable compounds of protein or other nature comprising active amine groups in its composition. The methods have great practical importance in providing for the pharmaceutical production long-acting medicinal preparations that are in great demand in the market of medicinal preparations, which can also be used for preparation of veterinary medicines. In perspective, the developed production processes can be widely used for solving a great many persistent problems in various economic sectors.

TABLE 1

Results of analytical monitoring of series of hyaluronidase conjugate with copolymer of N-oxide 1,4-ethylene piperazin and (N-carboxymethyl)-1,4-ethylene piperazin halogenide derived in EXAMPLES 1 through 10.

| Method of production | Enzyme activity at the time of production, IU/mg of drug | Enzyme activity after 1 year of storage*), IU/mg of drug | Enzyme activity decrease within 1 year, % | Conjugation degree, % | Target product yield, % | Production of medicinal preparation with Longidaza |
|---|---|---|---|---|---|---|
| EXAMPLE 1 | 221 | 212 | 4 | 85 | 86 | Suppositories |
| EXAMPLE 2 | 230 | 219 | 5 | 84 | 84 | Cream, ointment |
| EXAMPLE 3 | 242 | 230 | 5 | 86 | 87 | Injections |
| EXAMPLE 4 w/o urea | 168 | 123 | 27 | 65 | 74 | Injections |
| EXAMPLE 5 industrial | 235 | 221 | 6 | 85 | 87 | Suppositories, injections, cream, ointment |

TABLE 1-continued

Results of analytical monitoring of series of hyaluronidase conjugate with copolymer of N-oxide 1,4-ethylene piperazin and (N-carboxymethyl)-1,4-ethylene piperazin halogenide derived in EXAMPLES 1 through 10.

| Method of production | Enzyme activity at the time of production, IU/mg of drug | Enzyme activity after 1 year of storage*[)], IU/mg of drug | Enzyme activity decrease within 1 year, % | Conjugation degree, % | Target product yield, % | Production of medicinal preparation with Longidaza |
|---|---|---|---|---|---|---|
| batch 4, kg | | | | | | |
| EXAMPLE 6 | 265 | 254 | 4 | 96 | 97 | Suppositories |
| EXAMPLE 7 | 280 | 266 | 5 | 99 | 98 | Cream |
| EXAMPLE 8 | 275 | 264 | 4 | 99 | 98 | Injections |
| EXAMPLE 9 w/o urea | 175 | 133 | 24 | 85 | 82 | Injections |
| EXAMPLE 10 industrial batch 4, kg | 289 | 272 | 6 | 97 | 95 | Suppositories, injections, cream, ointment |

*[)]Storage at t = 2 to 8° C.

TABLE 2

Study of stability during long-term storage of Longizada ® produced with urea use (EXAMPLE 3 and EXAMPLE 8) and without urea use (EXAMPLE 9) as per 'cell-free protein' (Protein S) parameter.

| | Cell-free protein, % | | | | |
|---|---|---|---|---|---|
| Method of production | at the time of production | 3 months | 6 months | 9 months | 12 months |
| EXAMPLE 3 | 14 | 15 | 16 | 16 | 17 |
| EXAMPLE 8 | 1 | 1 | 2 | 2 | 3 |
| EXAMPLE 9 (w/o urea) | 15 | 26 | 30 | 32 | 33 |

The invention claimed is:

1. A method for making a biologically active conjugate of hyaluronidase enzyme, the method comprising:
conjugating hyaluronidase enzyme with a random water-soluble copolymer to obtain a liquid comprising a conjugate of hyaluronidase enzyme with the copolymer;
removing impurities from the liquid; and
freeze-drying the liquid,
wherein the water-soluble copolymer
is of a general formula:

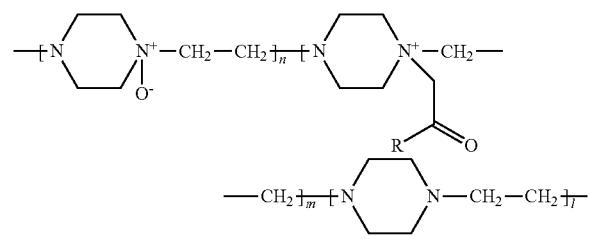

R = OH or NHNH$_2$ wherein n+m+l is the total number of units in the copolymer;
wherein n is from 40% to 90% of the total number of units in the copolymer; and
wherein m is from 3 to 40% of the total number of units in the copolymer,
obtaining the copolymer by:
oxidation of poly-1,4-ethylene piperazine by adding urea and an oxidizing agent that causes a release of oxygen to obtain an N-oxide of the poly-1,4-ethylene piperazine; and
alkylation of the N-oxide of the poly-1,4-ethylene piperazine by adding a lower haloalkane acid or an alkyl ester of a lower haloalkane acid,
wherein the conjugate comprises:
the N-oxide of the 1,4-ethylene piperazine; and
(N-carboxymethyl)-1,4-ethylene piperazine halogenide.

2. The method of claim 1, wherein the oxidation comprises adding 1 to 10% of the urea per total mass of a reaction mixture, including water.

3. The method of claim 1, wherein the conjugating comprises adding hyaluronidase taken from seminal glands of animals.

4. The method of claim 1, further comprising cleaning the copolymer by washing the copolymer with purified water.

5. A method of making a biologically active conjugate of hyaluronidase enzyme, the method comprising:
conjugating hyaluronidase enzyme with a random water-soluble copolymer to obtain a liquid comprising a conjugate of hyaluronidase enzyme with the copolymer;
removing impurities from the liquid;
concentrating the liquid; and
diluting or freeze-drying the liquid,
wherein the water-soluble copolymer
is of a general formula:

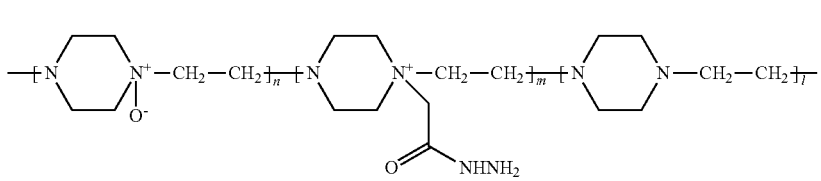

wherein n+m+1 is the total number of units in the copolymer;
where n is from 40% to 90% of the total number of units in the copolymer;
m is from 3 to 20% of total number of units in the copolymer;
obtaining the copolymer by:
  oxidation of poly-1,4-ethylene piperazine by adding urea and an oxidizing agent that causes a release of oxygen to obtain an N-oxide of poly-1,4-ethylene piperazine, and
  alkylation by adding an alkyl ether of haloalkane acid, in combination with hydrazinolysis of the N-oxide of poly-1,4-ethylene piperazine,
wherein the conjugate comprises:
the N-oxide of the 1,4-ethylene piperazine and
(N-carboxymethyl)-1,4-ethylene piperazine halogenide.

6. The method of claim 5, wherein the oxidation comprises adding 1 to 10% of the urea per total mass of reaction mixture, including water.

7. The method of claim 5, further comprising washing the copolymer with purified water after each of the oxidation, the alkylation, the hydrazinolysis, and the conjugation.

8. The method of claim 5, wherein the conjugating is carried out at temperatures ranging from 0 to 25° C.

9. A method of making a biologically active conjugate of hyaluronidase enzyme, the method comprising:
conjugating hyaluronidase enzyme with a random water-soluble copolymer to obtain a liquid comprising a conjugate of hyaluronidase enzyme with the copolymer,
removing impurities from the liquid,
diluting or concentrating the liquid,
freeze-drying the liquid;
wherein the water-soluble copolymer is of general formula:

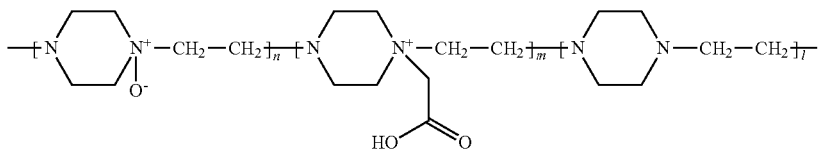

wherein n+m+1 is the total number of units in the copolymer;
where n is from 40% to 90% of the total number of units in the copolymer;
m is from 3 to 40% of the total number of units in the copolymer;
obtaining the copolymer by:
  oxidation of poly-1,4-ethylene piperazine by adding urea and an oxidizing agent that causes a release of oxygen to obtain an N-oxide of the poly-1,4-ethylene piperazine in an aqueous solution; and
  alkylation of the N-oxide of the poly-1,4-ethylene piperazine in the aqueous solution by adding a lower haloalkane acid,
wherein the conjugate comprises:
  the N-oxide of the 1,4-ethylene piperazine and
  (N-carboxymethyl)-1,4-ethylene piperazine halogenide.

10. The method of claim 9, wherein the oxidation comprises adding 1 to 10% of the urea per total mass of a reaction mixture, including water.

11. The method of claim 9, further comprising adding purified water after the conjugation and after the obtaining of the copolymer.

12. The method of claim 9, wherein the conjugating comprises adding a water-soluble carbodiimide in an amount from 3 to 50 wt % to a reaction mixture.

13. A medicinal preparation in a form of a suppository, ointment, injection, or cream, the medicinal preparation comprising the hyaluronidase enzyme conjugate made by the method of claim 1.

14. A medicinal preparation in a form of a suppository, ointment, injection, or cream, the medicinal preparation comprising the hyaluronidase enzyme conjugate made by the method of claim 5.

15. A medicinal preparation in a form of a suppository, ointment, injection, or cream, the medicinal preparation comprising the hyaluronidase enzyme conjugate made by the method of claim 9.

* * * * *